(12) United States Patent
Duan et al.

(10) Patent No.: US 12,352,730 B1
(45) Date of Patent: Jul. 8, 2025

(54) THREE-DIMENSIONAL WATER-ABSORPTION SWELLING MULTIFUNCTIONAL EXPERIMENTAL MACHINE AND METHOD FOR CHEMICAL SWELLING ROCKS

(71) Applicants: Shandong University, Jinan (CN); China University of Mining and Technology (Beijing), Beijing (CN)

(72) Inventors: Kang Duan, Jinan (CN); Yang Zheng, Jinan (CN); Ziyi Geng, Jinan (CN); Qiangyong Zhang, Jinan (CN); Qingrong Xiong, Jinan (CN); Di Wang, Jinan (CN); Qifang Liu, Jinan (CN); Luchao Wang, Jinan (CN); Dejun Liu, Jinan (CN)

(73) Assignee: Shandong University, Jinan (CN)

( * ) Notice: Subject to any disclaimer, the term of this patent is extended or adjusted under 35 U.S.C. 154(b) by 0 days.

(21) Appl. No.: 19/021,083

(22) Filed: Jan. 14, 2025

(30) Foreign Application Priority Data

Mar. 5, 2024 (CN) .......................... 202410249095.4

(51) Int. Cl.
*G01N 3/18* (2006.01)
*G01N 3/02* (2006.01)
*G01N 33/24* (2006.01)

(52) U.S. Cl.
CPC ................. *G01N 3/18* (2013.01); *G01N 3/02* (2013.01); *G01N 33/24* (2013.01);
(Continued)

(58) Field of Classification Search
CPC ............ G01N 3/36; G01N 15/08; G01N 3/08; G01N 3/32; G01N 15/0806; G01N 24/081;
(Continued)

(56) References Cited

U.S. PATENT DOCUMENTS

2022/0390339 A1* 12/2022 Shi ......................... G01N 33/24

FOREIGN PATENT DOCUMENTS

CN 212658548 U * 3/2021
CN 111579343 B * 5/2023 ............. G01N 1/286

OTHER PUBLICATIONS

Notice of Allowance for CN 202410249095.4 from CNIPA.
(Continued)

*Primary Examiner* — Brandi N Hopkins

(57) ABSTRACT

The present invention relates to the field of rock mechanics technology, and provides a three-dimensional water absorption swelling multifunctional experimental machine and method for chemical swelling rock, comprising a triaxial high-temperature and high-pressure reaction chamber, the triaxial high-temperature and high-pressure reaction chamber is respectively connected with a confining pressure loading controller, a water pressure loading controller, a temperature controller, an axial pressure loading controller, a pH value monitor and a data acquisition and analyzer; the triaxial high-temperature and high-pressure reaction chamber includes a set of internal cavity and an external cavity, a sealing liner sleeve is provided between the internal cavity and the external cavity, a rock sample is provided in the internal cavity, a water-permeable pressure hoop is provided outside the rock sample, and the sealing liner sleeve is connected with a circumferential stress-strain sensor through a displacement structure.

9 Claims, 6 Drawing Sheets

(52) U.S. Cl.
CPC ............... *G01N 2203/0226* (2013.01); *G01N 2203/0232* (2013.01); *G01N 2203/0236* (2013.01); *G01N 2203/0246* (2013.01); *G01N 2203/0682* (2013.01)

(58) Field of Classification Search
CPC ........ G01N 1/42; G01N 1/286; G01N 23/046; G01N 15/082; G01N 13/04; G01N 3/02; G01N 3/062; G01N 15/0826; G01N 3/62; G01N 22/00; G01N 25/20; G01N 3/10; G01N 3/04; G01N 3/24; G01N 7/04; G01N 33/00; G01N 17/02; G01N 1/00; G01N 3/307; G01N 15/0893; G01N 2203/0256; G01N 3/06; Y02A 90/30
USPC .............................. 73/785, 783, 786–88, 799
See application file for complete search history.

(56) References Cited

OTHER PUBLICATIONS

First Examination for CN 202410249095.4 from CNIPA.
Zheng, "Improvement and Research for Free Swelling Rate Test of Rock," Railway Consturction Technology, 1009-4539 (2023) 01-0016-04.
Huang, "Characteristics of Expansive Rock and Its Effect on Tunnel Stability," Jounal of Railway Engineering Society, Mar. 2001 No. 1 (Ser. 69).

\* cited by examiner

(12) United States Patent

THREE-DIMENSIONAL WATER-ABSORPTION SWELLING MULTIFUNCTIONAL EXPERIMENTAL MACHINE AND METHOD FOR CHEMICAL SWELLING ROCKS

CROSS-REFERENCE TO RELATED APPLICATIONS

The present application claims the priority of Chinese patent application entitled "A three-dimensional water-absorption swelling multifunctional experimental system and method for chemical swelling rocks" submitted on Mar. 5, 2024, with the application number of 202410249095.4, the entire contents of which are incorporated herein by reference.

TECHNICAL FIELD

The present invention relates to the technical field of rock mechanics, and in particular to a three-dimensional water-absorption swelling multifunctional experimental machine and method for chemical swelling rocks.

BACKGROUND OF THE PRESENT INVENTION

Chemical swelling rocks are widely distributed in China. This type of rock formation has the development characteristics of stratification, heterogeneity and discontinuity. After absorbing water, it will have typical characteristics of volumetric swelling, getting softened and being susceptible to ion corrosion. When underground projects pass through chemical swelling rock formations with chemical swelling, the non-uniform swelling force and swelling deformation generated by the water absorption of this type of rock formation will have a significant squeezing effect on the underground structure, causing partial deformation, cracking, uplift and other diseases of the underground structure, which brings great hidden dangers to the safe construction and operation & maintenance of the underground structure. Therefore, it is very necessary to study the swelling and deformation laws of chemical swelling rocks in complex environments.

For the experimental study of the swelling characteristics of chemical swelling rocks, conventional consolidators and dilatometers for swelling soils are usually used to carry out free swelling tests and lateral swelling tests. The swelling laws measured by these two conventional instruments are difficult to apply to actual projects. Their shortcomings are mainly reflected in three aspects: firstly, conventional consolidators or dilatometers usually adopt a one-dimensional water absorption, that is, permeable plates are used at the upper and lower ends of the sample for percolation of water, which can only monitor the axial stress-strain of the sample. Although there are relatively few three-dimensional water-absorption swelling test devices, the sample is generally simplified into a square block and the effect of confining pressure is not considered due to the water sealing effect and sensor oscillation. In other words, the confining pressure and water pressure as a disturbance force will make the built-in sensor unable to be stably fixed. When the water pressure is greater than the confining pressure, it will cause the built-in sensor to collapse outward. Secondly, limited by the reaction chamber of conventional consolidators or dilatometers, only single-field simple swelling tests can be carried out. Even if complex rock swelling instruments have been available today, they can only achieve tests in a dual-field coupling environment, and are unable to support the rock sample swelling tests under multi-field coupling conditions of confining pressure, axial pressure, water pressure and temperature. In addition, existing instruments can only measure a single mechanical parameter, stress or strain, and cannot measure multiple parameters such as stress, strain, and ion concentration gradient.

Therefore, in order to better simulate the multi-field coupling effects on chemical swelling rocks in complex environments, the present invention provides a three-dimensional water-absorption swelling multifunctional experimental machine and method for chemical swelling rocks to solve the above-mentioned problems existing in current research due to instrument limitations.

SUMMARY OF PRESENT INVENTION

In order to solve the problems existing in the background art, the present invention provides a three-dimensional water-absorption swelling multifunctional experimental machine and method for chemical swelling rocks. The experimental device in the present invention can not only simultaneously provide a test environment of confining pressure, axial pressure, water pressure, high temperature and three-dimensional water absorption, realize true simulation of the complex occurrence environment of chemical swelling rocks, but also ensure that the sensor captures the sample data stably and accurately.

To achieve the above object, the present invention adopts the following solutions:

a three-dimensional water-absorption swelling multifunctional experimental machine for chemical swelling rocks, comprising a triaxial high-temperature and high-pressure reaction chamber, wherein the triaxial high-temperature and high-pressure reaction chamber is respectively connected with a confining pressure loading controller, a water pressure loading controller, a temperature controller, an axial pressure loading controller, a pH value monitor and a data acquisition and analyzer;

the triaxial high-temperature and high-pressure reaction chamber comprises an upper end cover and a lower end cover which are detachable at upper and lower ends; an internal cavity and an external cavity are provided between the upper end cover and the lower end cover; the external cavity is sleeved outside the internal cavity; a sealing liner sleeve is provided between the internal cavity and the external cavity; an upper convex body and a lower convex body protruding toward one side of the external cavity are provided at upper and lower ends of the sealing liner sleeve; an oil cavity is provided between the upper convex body and the lower convex body; and force transmission pads are provided between the upper convex body and the upper end cover and between the lower convex body and the lower end cover;

a rock sample is provided in the internal cavity, and a water-permeable pressure hoop is arranged outside the rock sample, the outer wall of the water-permeable pressure hoop is in close contact with the sealing liner sleeve, and the sealing liner sleeve is connected to a circumferential stress-strain sensor via a displacement structure; an upper pressure head is arranged above the rock sample, a water outlet pipe connected to the rock sample is arranged in the upper pressure head, a lower pressure head is arranged below the rock sample, a water inlet pipe connected to the rock sample is arranged in the lower pressure head, and an axial pressure loading screw pressure head is detachably connected to the top of the upper pressure head; the water-permeable pressure hoop comprises a plurality of sections of hoop bodies with joints, and the hoop bodies are respectively provided with axial water-passing grooves and radial water-passing holes.

Further, an upper limit sleeve is movably connected between the upper pressure head and the sealing liner sleeve, the upper limit sleeve corresponds to the water-permeable pressure hoop up and down and extends upward to the upper end cover, and a lower limit sleeve is movably connected between the lower pressure head and the sealing liner sleeve, and the lower limit sleeve extends downward to the lower end cover.

Further, the upper pressure head extends out of the upper end cover, an upper permeable stone is provided between the upper pressure head and the rock sample, and a lower permeable stone is provided between the lower pressure head and the rock sample; one end of the water outlet pipe is connected to the upper permeable stone, and the other end is connected to the pH value monitor through a first flow meter and a first fluid pressure gauge, and one end of the water inlet pipe is connected to the lower permeable stone, and the other end is connected to the water pressure loading controller and the water pump through a second flow meter and a second fluid pressure gauge.

Further, an annular ion concentration sensor and a heating coil are sleeved over the rock sample, the heating coil is connected to the temperature controller, and the annular ion concentration sensor and the circumferential stress-strain sensor are connected to the data acquisition and analyzer.

Further, the displacement structures are provided in plurality, the circumferential stress-strain sensor corresponds to the displacement structures one by one, and the plurality of displacement structures are evenly distributed circumferentially on the side wall of the sealing liner sleeve.

Further, the displacement structure comprises a compression cavity, holes are provided at both ends of the compression cavity, a displacement rod is provided in the compression cavity, both ends of the displacement rod extend out of the holes, one end of the displacement rod is in close contact with the sealing liner sleeve, and the other end is connected to the circumferential stress-strain sensor via a connecting plate, a portion of the displacement rod located in the compression cavity is provided with a convex body and a force adjustment spring, the convex body is located on the side close to the sealing liner sleeve, the force adjustment spring is sleeved on the non-convex body portion of the displacement rod, and the outer diameter of the convex body is greater than the radial dimension of the hole.

Further, an oil inlet and an oil outlet are arranged opposite each other on the outer wall of the triaxial high-temperature and high-pressure reaction chamber, the oil inlet and the oil outlet are internally connected to the oil cavity, and the oil inlet and the oil outlet are externally connected to the confining pressure loading controller; and an exhaust port communicating with the outside is arranged on the external cavity.

Further, the axial pressure loading screw pressure head is connected to the axial pressure loading controller, the axial pressure loading screw pressure head is arranged above the upper pressure head through a reaction frame, the axial pressure loading screw pressure head is also connected to an axial sensor, and the axial sensor is connected to the data acquisition and analyzer.

Further, the experimental machine also comprises an operating table, on which a feeding pad is detachably fixed, and the feeding pad is arranged below the triaxial high-temperature and high-pressure reaction chamber by connecting with the lower end cover, and a moving wheel is provided at the lower part of the feeding pad; the reaction frame is fixed on the operating table.

A three-dimensional water-absorption swelling multi-functional experimental method for chemical swelling rocks, comprising the following steps:

step 1: process the water-permeable pressure hoop according to the swelling test type of the rock sample: when conducting a lateral restraint swelling rate test, use high-strength glue to bond the multiple sections of the hoop bodies with joints; when conducting a free swelling rate test and a swelling test under different confining pressure and water pressure conditions, there is no need to process the water-permeable pressure hoop;

step 2: place the triaxial high-temperature and high-pressure reaction chamber containing the rock sample below the axial pressure loading screw pressure head through the feeding pad, so that the axial pressure loading screw pressure head is directly opposite to the upper pressure head;

step 3: open the water pressure loading controller to add water, so that the water passes vertically through the lower permeable stone, the rock sample, and the upper permeable stone from the water inlet pipe, and passes horizontally through the rock sample and the water-permeable pressure hoop to achieve three-dimensional immersion of the rock sample, open the exhaust port, and close the exhaust port when there is no residual air in the triaxial high-temperature and high-pressure reaction chamber;

step 4: set the axial pressure, water pressure and temperature according to the test plan, and carry out the swelling rate test of the rock sample under different axial pressure, confining pressure, water pressure and temperature coupling conditions.

The present invention has the following beneficial effects:

compared with the existing rock swelling testing instruments, the triaxial high-temperature and high-pressure reaction chamber of the present invention is connected with a confining pressure loading controller, a water pressure loading controller, a temperature controller, an axial pressure loading controller, a pH value monitor and a data acquisition and analyzer; a multi-section water-permeable pressure hoop with an axial water-passing groove and a radial water-passing hole is arranged in the triaxial high-temperature and high-pressure reaction chamber, so that the three-dimensional water absorption swelling of the rock sample under the coupling conditions of confining pressure, axial pressure, water pressure and temperature is realized, thereby the complex formation environment where the swelling rock exists is more realistically simulated.

Moreover, the present invention arranges a circumferential stress-strain sensor on the side of the rock sample to test the lateral swelling stress or strain of the rock. The circumferential stress-strain sensor is indirectly connected to the rock sample through a displacement structure, which can eliminate the disturbance effect of the confining pressure and water pressure on the circumferential stress-strain sensor. A plurality of displacement structures are evenly distributed circumferentially on the side wall of the sealing liner sleeve, thereby realizing three-dimensional high-precision measurement of volumetric swelling strain-stress in the water-absorption swelling process of the rock sample.

Secondly, an annular ion concentration sensor connector is closely sleeved over the rock sample, and the water outlet is connected to the pH value monitor, which can dynamically monitor the ion transport and diffusion process after internal dissolution of the sample and obtain the changing law of water acidity and alkalinity.

In addition, the machine in the present invention has various functions and can be applied to carry out various swelling characteristic tests of swelling rocks, mainly including free swelling rate test, lateral constraint swelling rate test under different axial pressures, as well as swelling rate and swelling force tests under different confining pressure, water pressure, axial pressure and temperature coupling conditions.

Numbers in figures: 1. upper end cover; 2. lower end cover; 3. external cavity; 4. sealing liner sleeve; 5. upper convex body; 6. lower convex body; 7. oil cavity; 8. force transmission pad; 9. rock sample; 10. water-permeable pressure hoop; 11. Force adjustment spring; 12. circumferential stress-strain sensor; 13. water outlet pipe; 14. upper pressure head; 15. water inlet pipe; 16. lower pressure head; 17. axial pressure loading screw pressure head; 18. hoop body; 19. axial water-passing groove; 20. radial water-passing hole; 21. upper limit sleeve; 22. upper permeable stone; 23. lower permeable stone; 24. lower limit sleeve; 25. displacement rod; 26. first flow meter; 27. first fluid pressure gauge; 28. second flow meter; 29. second fluid pressure gauge; 30. heating coil; 31. annular ion concentration sensor; 32. connecting plate; 33. oil inlet; 34. oil outlet; 35. exhaust port; 36. axial sensor; 37. operating table; 38. feeding pad; 39. reaction frame; 40. triaxial high-temperature and high-pressure reaction chamber; 41. confining pressure loading controller; 42. water pressure loading control component; 43. temperature controller; 44. axial pressure loading controller; 45. pH value monitor; 46. data acquisition and analyzer; 47. oil pipe; 48. water pipe; 49. compression cavity.

DETAILED DESCRIPTION OF PREFERRED EMBODIMENTS

In order to make the present invention clearer and more understandable, it is further described in detail below in conjunction with the drawings and embodiments. It should be understood that the given embodiment is only one implementation method and does not represent all embodiments.

Figure 1:
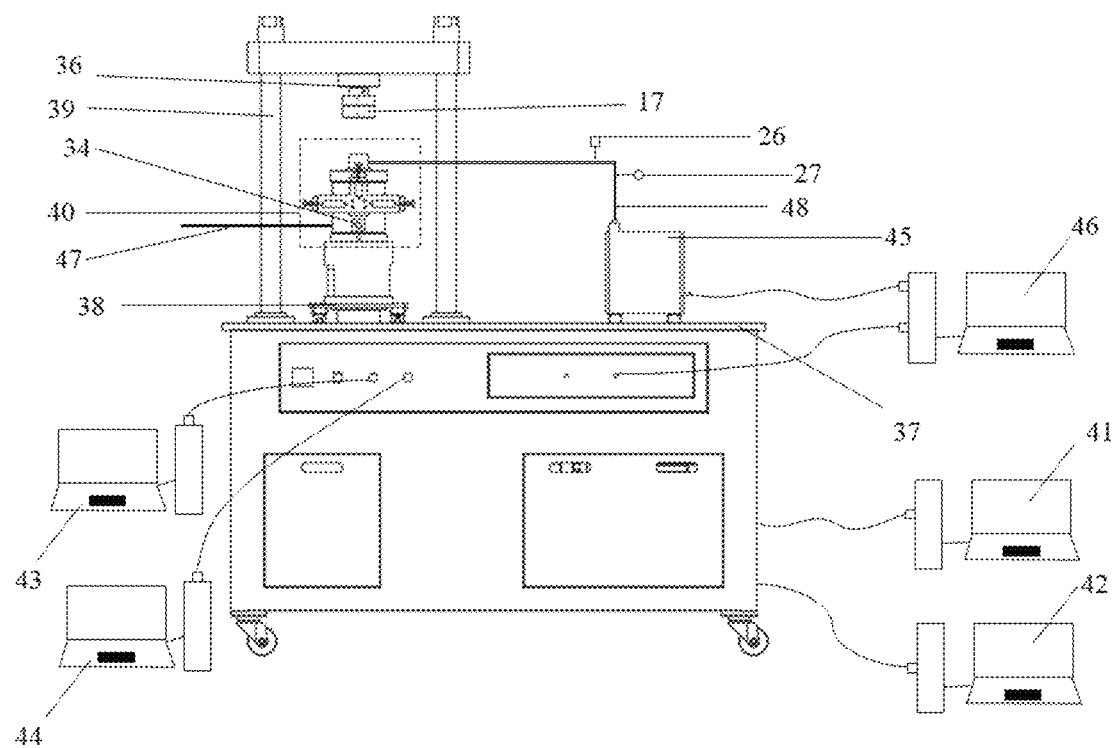
FIG. 1 is a front view of the three-dimensional water-absorption swelling multifunctional experimental machine for chemical swelling rocks according to the present invention.
Figure 2:
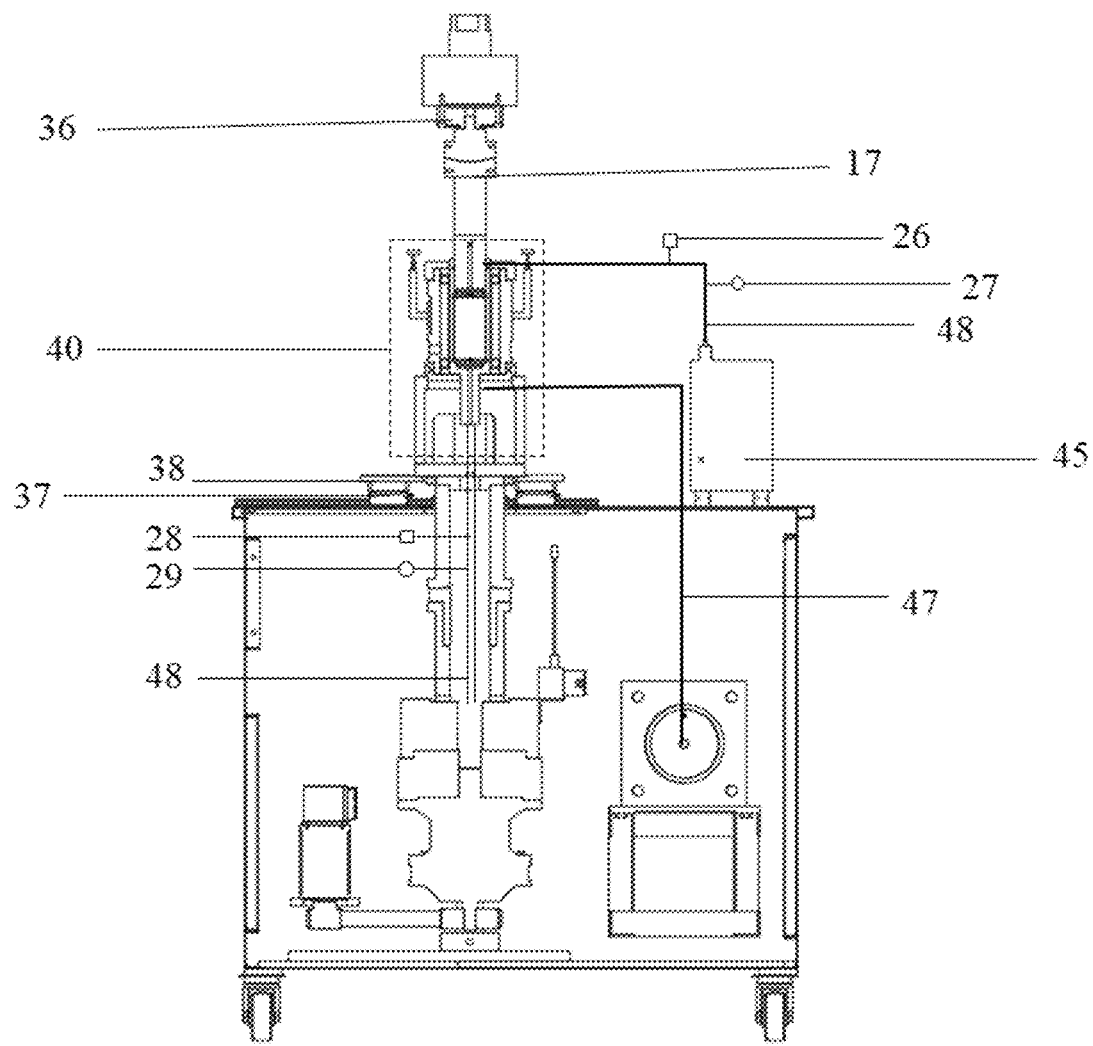
FIG. 2 is a schematic cross-sectional view of the three-dimensional water-absorption swelling multifunctional experimental machine for chemical swelling rocks according to the present invention.
Figure 3:
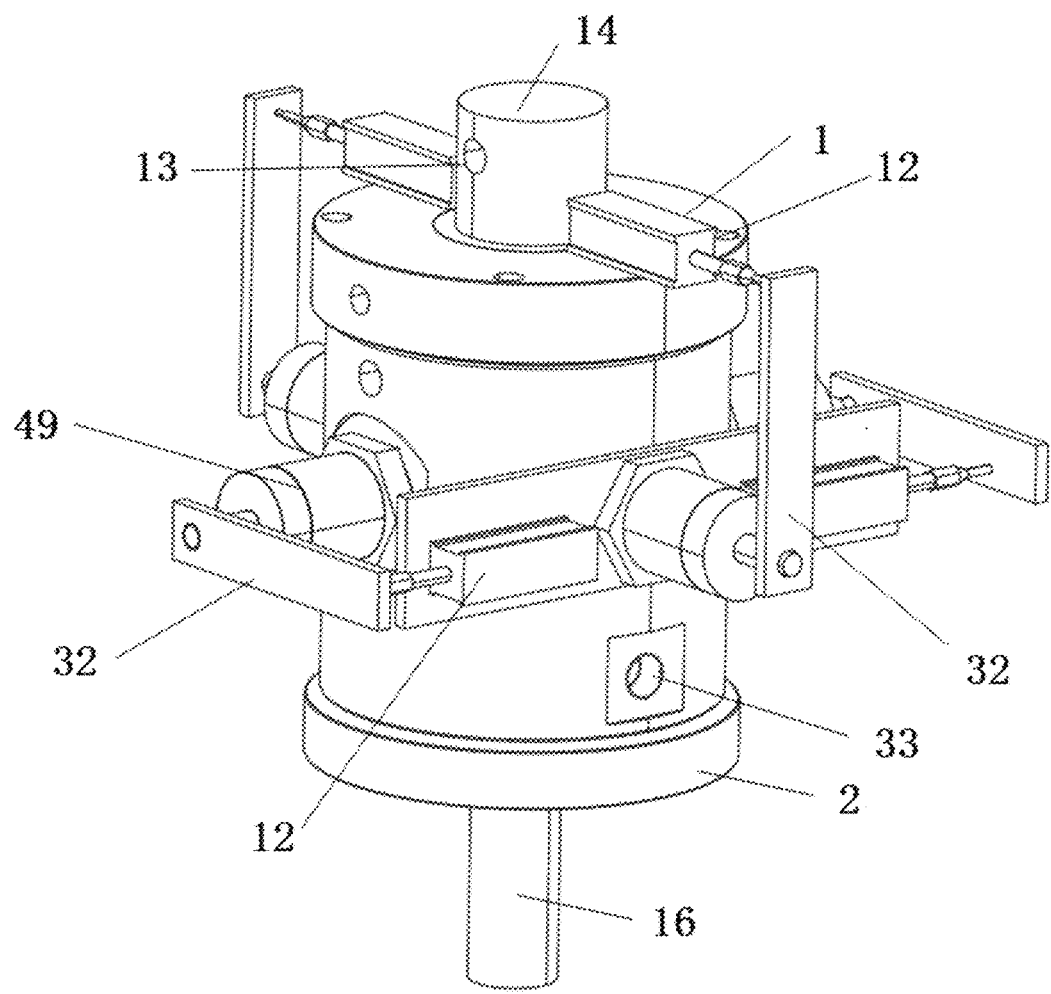
FIG. 3 is a schematic diagram of the overall structure of the triaxial high-temperature and high-pressure reaction chamber according to the present invention.
Figure 4:
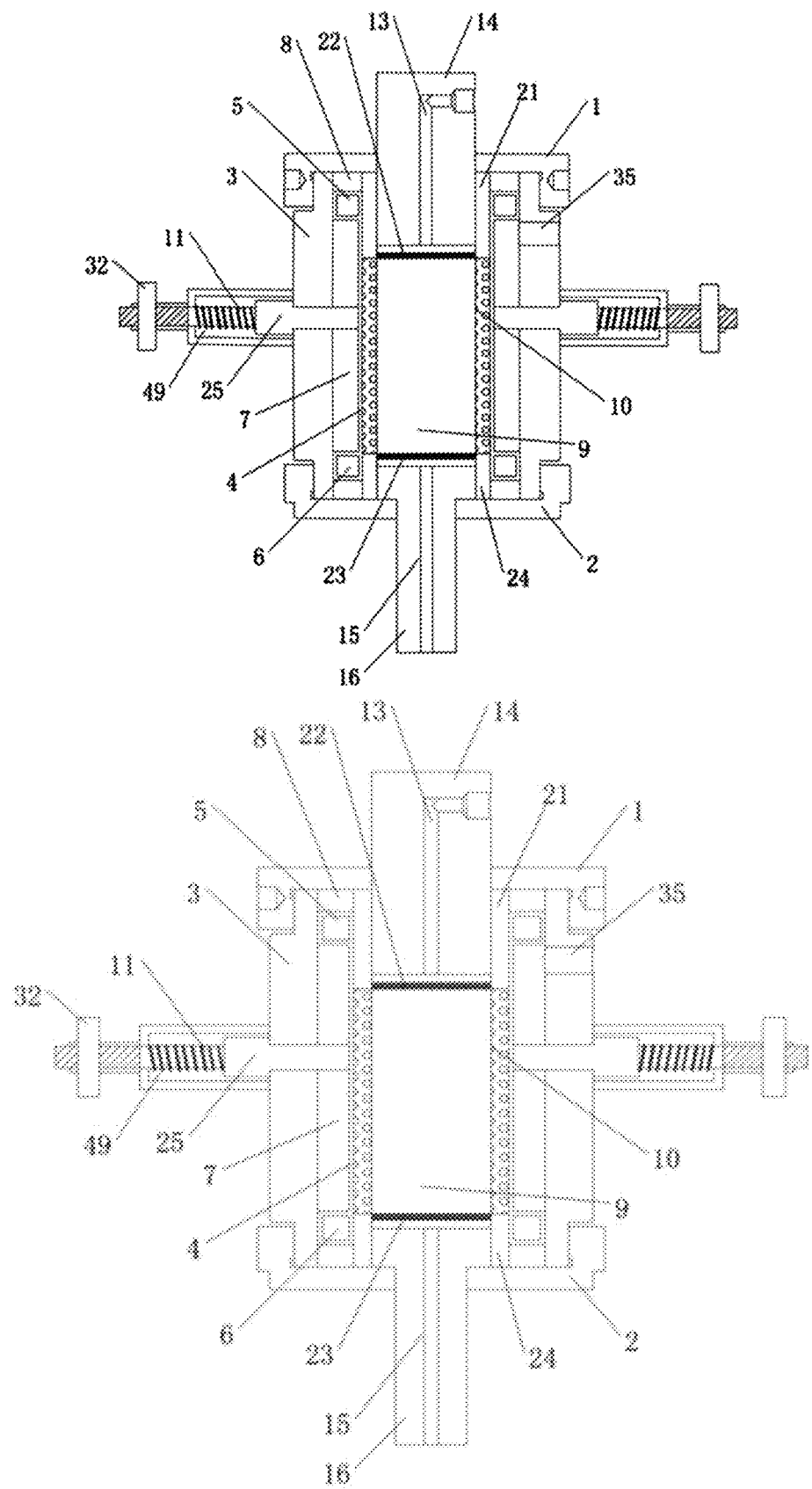
FIG. 4 is a schematic cross-sectional view of the structure of the triaxial high-temperature and high-pressure reaction chamber according to the present invention.
Figure 5:
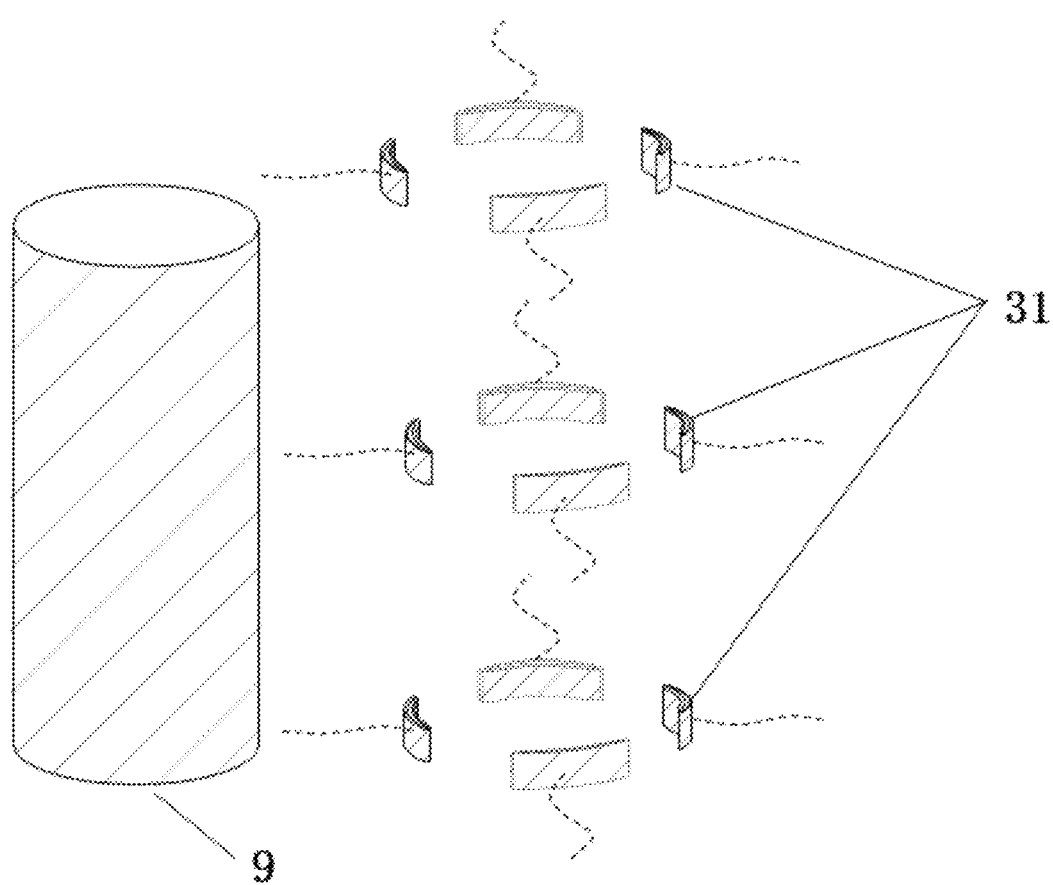
FIG. 5 is a schematic diagram of the structure of the rock sample annular ion sensor according to the present invention.
Figure 6:
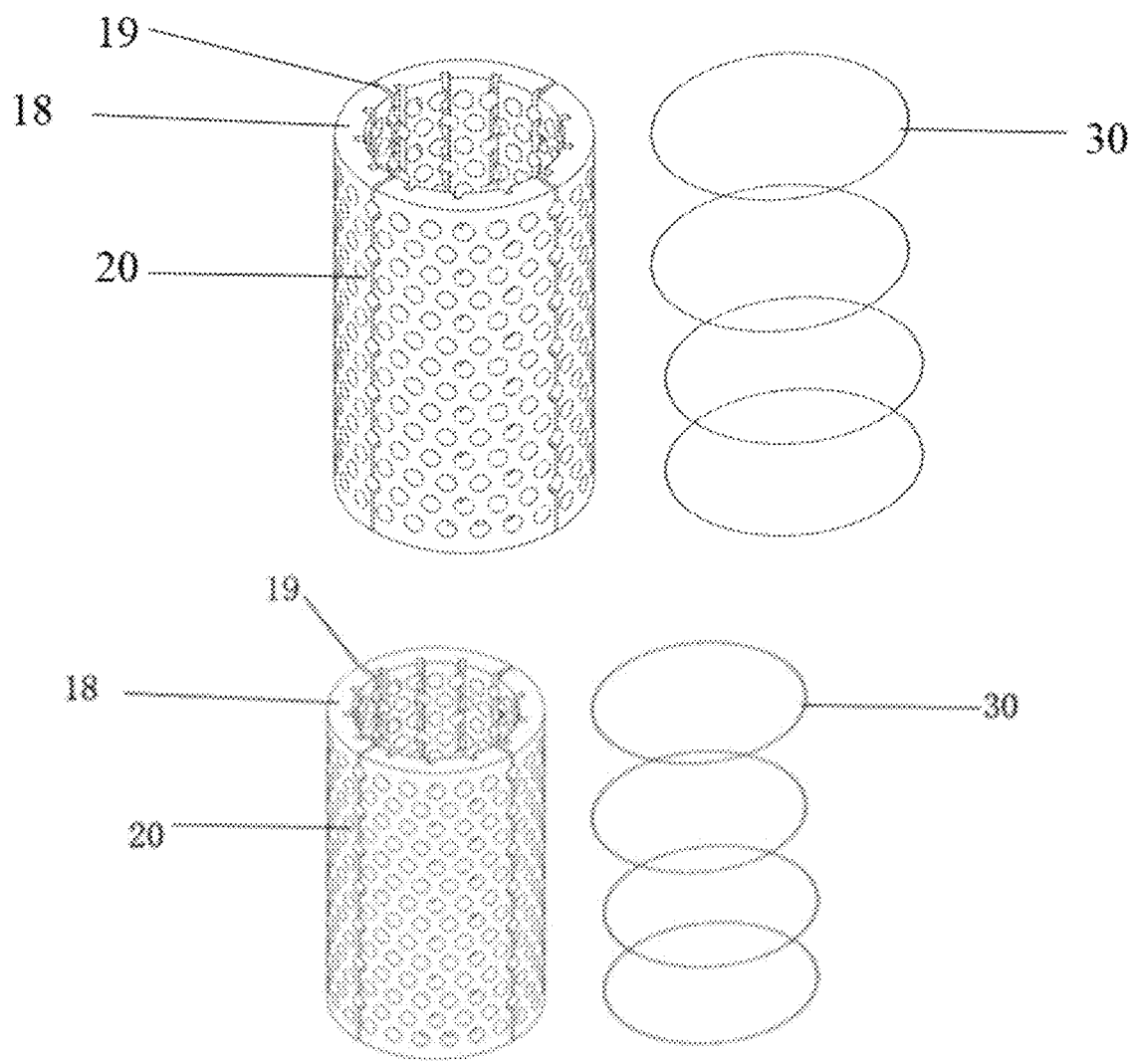
FIG. 6 is a schematic diagram of the structure of a water-permeable pressure hoop for a rock sample according to the present invention.

In conjunction with FIGS. 1 to 6, this embodiment provides a three-dimensional water-absorption swelling multifunctional experimental machine for chemical swelling rocks, comprising a triaxial high-temperature and high-pressure reaction chamber 40, which is connected respectively to a confining pressure loading controller 41, a water pressure loading controller 42, a temperature controller 43, an axial pressure loading controller 44, a pH value monitor 45, and a data acquisition and analyzer 46. The confining pressure loading controller 41 is used to provide confining pressure to the rock sample 9; the axial pressure loading controller 44 is used to provide axial pressure to the rock sample 9; the water pressure loading controller 42 is used to provide water pressure to the rock sample 9; the temperature controller 43 is used to provide a high-temperature environment to the rock sample 9; the pH value monitor 45 is used to monitor the changes in water acidity and alkalinity caused by the dissolution of the rock sample 9; and the data acquisition and analyzer 46 is used to collect experimental data in the three-dimensional water absorption swelling process of the rock sample 9.

The triaxial high-temperature and high-pressure reaction chamber 40 comprises an upper end cover 1 and a lower end cover 2 which are detachable at the upper and lower ends respectively. The upper end cover 1 and the lower end cover 2 are connected to the triaxial high-temperature and high-pressure reaction chamber 40 through a plurality of vertical bolts for easy disassembly. Water-tight gaskets are arranged at the bottom of the vertical bolts to improve the sealing property of the test chamber. An internal cavity and an external cavity 3 are arranged between the upper end cover 1 and the lower end cover 2. The external cavity 3 is sleeved outside the internal cavity. An exhaust port 35 communicating with the outside is arranged on the external cavity 3 for exhausting the air in the reaction chamber to facilitate the entry of the fluid.

A sealing liner sleeve 4 is provided between the internal cavity and the external cavity 3, and an upper convex body 5 and a lower convex body 6 protruding toward one side of the external cavity 3 are respectively provided at the upper and lower ends of the sealing liner sleeve 4, an oil cavity 7 is provided between the upper convex body 5 and the lower convex body 6, and force transmission pads 8 are provided between the upper convex body 5 and the upper end cover 1 and between the lower convex body 6 and the lower end cover 2.

Specifically, the sealing liner sleeve 4 is a rubber sealing liner sleeve 4, which can transmit the confining pressure and provide the oil-water isolation environment. The upper convex body 5 and the lower convex body 6 of the sealing liner sleeve 4 can increase the fixed area of the sealing liner sleeve 4, so that the upper and lower end surfaces of the sealing liner sleeve 4 are fixed, preventing the sealing liner sleeve 4 from moving up and down.

An oil inlet 33 and an oil outlet 34 are arranged opposite each other on the outer wall of the triaxial high-temperature and high-pressure reaction chamber 40. The oil inlet 33 and the oil outlet 34 are connected to the oil cavity 7, and the oil inlet 33 and the oil outlet 34 are connected to the confining pressure loading controller 41. The oil inlet 33 and the oil outlet 34 are connected to the oil pump through the oil pipe 47. During the test, the oil pump pumps the oil into the oil pipe 47, then inputs the oil into the oil cavity 7 through the oil inlet 33, and applies lateral pressure, i.e., confining pressure into the internal cavity through the sealing liner sleeve 4. The oil cavity 7 also generates upper and lower pressures. The upper and lower pressures squeeze the upper convex body 5 and the lower convex body 6, and are led out of the triaxial high-temperature and high-pressure reaction chamber 40 through the cooperation of the force transmission pad 8. The force transmission pad 8 is made of a metal material, like stainless steel, which can prevent the corrosion of the force transmission pad 8.

A rock sample 9 is provided in the internal cavity, and a water-permeable pressure hoop 10 is sleeved over the rock sample 9. The outer wall of the water-permeable pressure hoop 10 is in close contact with the sealing liner sleeve 4, and the sealing liner sleeve 4 is connected to a circumferential stress-strain sensor through a displacement structure; an upper pressure head 14 is provided above the rock sample 9, and a water outlet pipe 13 connected to the rock sample 9 is provided in the upper pressure head 14, and a lower pressure head 16 is provided below the rock sample 9, and a water inlet pipe 15 connected to the rock sample 9 is provided in the lower pressure head 16, and an axial pressure loading screw pressure head 17 is detachably connected to the top of the upper pressure head 14; the water-permeable pressure hoop 10 includes a plurality of sections of hoop bodies 18 with joints, and an axial water-passing groove 19 and a radial water-passing hole 20 are respectively provided on the hoop bodies 18.

Specifically, the upper pressure head 14 extends out of the upper end cover 1, an upper permeable stone 22 is provided between the upper pressure head 14 and the rock sample 9, and a lower permeable stone 23 is provided between the lower pressure head 16 and the rock sample 9; one end of the water outlet pipe 13 is connected to the upper permeable stone 22, and the other end is connected to the pH value monitor 45 through the first flow meter 26 and the first fluid pressure gauge 27; one end of the water inlet pipe 15 is connected to the lower permeable stone 23, and the other end is connected to the water pressure loading controller 42 and the water pump through the second flow meter 28 and the second fluid pressure gauge 29. The pressure and flow at the water outlet and the water inlet can be monitored by the first flow meter 26 and the first fluid pressure gauge 27, the second flow meter 28 and the second fluid pressure gauge 29, and the pressure or flow required for the test can be conveniently adjusted. The water inlet pipe 15 can be connected to the water pump over a long distance through the water pipe 48. The upper permeable stone 22 and the lower permeable stone 23 can prevent the debris produced by rock dissolution from clogging the water outlet pipe 13 and the water inlet pipe 15 on the one hand, and can make water evenly enter and flow out of the rock sample 9 on the other hand. The upper pressure head 14 extends out of the upper end cover 1, which is convenient for the axial pressure loading screw pressure head 17 to load the axial force downward thereon. The lower pressure head 16 has the function of entering the water body and blocking, and does not need to load pressure, so it can extend out of the lower end cover 2 or extend into the lower end cover 2. The lower pressure head 16 in this embodiment is a T-shaped structure, which is convenient for fixing. The upper pressure head 14 is a cylindrical structure, which is convenient for taking out from the internal cavity during different tests.

The rock sample 9 is provided with an annular ion concentration sensor 31 and a heating coil 30 which are sleeved thereon, the heating coil 30 is connected to the temperature controller 43, and the annular ion concentration sensor 31 and the circumferential stress-strain sensor 12 are connected to the data acquisition and analyzer 46. The annular ion concentration sensor 31 is respectively arranged at the top, middle and bottom of the rock sample 9, and each of them is provided with 4 ion concentration sensor connectors, so as to realize the effective measurement of the ion concentration gradient around the rock sample 9. The heating coils 30 are evenly distributed on the side wall of the rock sample 9. In this embodiment, four heating coils 30 are provided with an external temperature controller 43, which can heat the water and simulate the water temperature of different depth formations.

Specifically, the water-permeable pressure hoop 10 includes a plurality of sections of hoop bodies 18 with joints, and the hoop bodies 18 are respectively provided with axial water-passing grooves 19 and radial water-passing holes 20, so as to realize three-dimensional immersion of the rock sample 9. Preferably, the water-permeable pressure hoop 10 of this embodiment is divided into four sections. According to the test type, the joints can be bonded with high-strength glue or not. If different confining pressure and water pressure swelling tests are carried out, no bonding is required. If the lateral constraint swelling rate test is carried out, high-strength glue bonding is required to realize the lateral constraint condition of the rock sample 9.

An upper limit sleeve 21 is movably connected between the upper pressure head 14 and the sealing liner sleeve 4. The upper limit sleeve 21 corresponds to the water-permeable pressure hoop 10 up and down and extends upward to the upper end cover 1. A lower limit sleeve 24 is movably connected between the lower pressure head 16 and the sealing liner sleeve 4. The lower limit sleeve 24 extends downward to the lower end cover 2. The upper limit sleeve 21 can limit the position of the upper pressure head 14 on the one hand, and protect the water-permeable pressure hoop 10 on the other hand to prevent the upper pressure head 14 from applying force to the water-permeable pressure hoop 10 when it moves downward. During the test, the upper limit sleeve 21 can be taken out from the internal cavity to facilitate the bonding of the water-permeable pressure hoop 10. It should be understood that in order to facilitate the fixing of the upper limit sleeve 21, the upper end of the upper limit sleeve 21 can extend into the upper end cover 1 or extend out of the upper end cover 1. Since the lower pressure head 16 does not need to apply pressure to the cavity, the lower limit sleeve 24 only serves to limit the position of the lower pressure head 16.

Specifically, the axial pressure loading screw pressure head 17 is connected to the axial pressure loading controller 44, and the axial pressure loading screw pressure head 17 is arranged above the upper pressure head 14 through the reaction frame 39. The axial pressure loading screw pressure head 17 is also connected to the axial sensor 36, and the axial sensor 36 is connected to the data acquisition and analyzer 46. The loading mode of the axial pressure loading screw pressure head 17 is determined by the axial pressure loading controller 44. During the test, the axial pressure loading screw pressure head 17 presses down the upper pressure head 14, and the loading speed or loading pressure of the upper pressure head 14 can be controlled to apply a certain axial pressure to the rock sample 9.

Specifically, the displacement structure is provided in plurality, and the circumferential stress-strain sensor 12 corresponds to the displacement structure one by one, and the plurality of displacement structures are evenly distributed on the side wall of the sealing liner sleeve 4 in the circumferential direction. The circumferential stress-strain sensor 12 monitors the stress-strain of the rock sample 9 through the displacement structure, avoiding the phenomenon that the sensor is in direct contact with the rock sample 9 and is prone to fall off during the test, thereby preventing the confining pressure and water pressure from disturbing the sensor when conducting an swelling test under the coupling conditions of confining pressure and water pressure, and realizing the accurate monitoring of the stress-strain of the rock sample 9 by the sensor. Preferably, in this embodiment, four displacement structures are provided, which are respectively arranged at different positions of the same cross section of the sealing liner sleeve 4, so that the swelling stress or strain in four directions can be measured to improve the accuracy of the data.

Specifically, the displacement structure includes a compression cavity 49, holes are provided at both ends of the compression cavity 49, a displacement rod 25 is provided in the compression cavity 49, both ends of the displacement rod 25 extend out of the holes, one end of the displacement rod 25 is in close contact with the sealing liner sleeve 4, and the other end is connected to the circumferential stress-strain sensor 12 through a connecting plate 32, and the portion of the displacement rod 25 located in the compression cavity 49 is provided with a convex body and a force adjustment spring 11, the convex body is located on a side close to the sealing liner sleeve 4, the force adjustment spring 11 is sleeved on the non-convex body portion of the displacement rod 25, and the outer diameter of the convex body is greater than the radial size of the hole. Preferably, one end of the connecting plate 32 is sleeved on the displacement rod 25, and the end portion where the displacement rod 25 is connected to the connecting plate 32 is set as a thread, and the connecting plate 32 and the displacement rod 25 are fixed together by a nut. The circumferential stress-strain sensor 12 is connected to the connecting plate 32 through a displacement meter. When the rock sample 9 absorbs water and displaces, the sealing liner sleeve 4 expands outward, causing the displacement rod 25 to move outward, thereby driving the connecting rod to move. The displacement meter can then measure its displacement, and the annular stress-strain sensor 12 can then obtain its stress-strain value. The circumferential stress-strain sensor adopts a non-destructive installation method. During installation, the vacuum suction cup at the bottom is directly adsorbed on the surface of the upper end cover 1 or the bracket.

The experimental machine also includes an operating table 37, on which a feeding pad 38 is detachably fixed, and the feeding pad 38 is arranged below the triaxial high-temperature and high-pressure reaction chamber 40 by connecting with the lower end cover 2, and a moving wheel is arranged at the lower part of the feeding pad 38, and the triaxial high-temperature and high-pressure reaction chamber 40 can be conveniently moved by the feeding pad 38. The reaction frame 39 is fixed on the operating table 37, and a crossbeam is arranged on the reaction frame 39, and an axial pressure loading screw pressure head 17 is arranged on the crossbeam, so as to facilitate the movement of the axial pressure loading screw pressure head 17 to apply pressure to the upper pressure head 14.

The present invention also provides a multifunctional experimental method for three-dimensional water absorption and swelling of chemical swelling rocks based on the above experimental machine, comprising the following steps:

step 1: process the water-permeable pressure hoop 10 according to the swelling test type of the rock sample 9: when conducting a lateral restraint swelling rate test, use high-strength glue to bond the multiple sections of hoop bodies 18 with joints; when conducting a free swelling rate test and a swelling test under different confining pressure and water pressure conditions, there is no need to process the water-permeable pressure hoop 10;

step 2: place the triaxial high-temperature and high-pressure reaction chamber 40 containing the rock sample 9 below the axial pressure loading screw pressure head 17 through the feeding pad 38, so that the axial pressure loading screw pressure head 17 is directly opposite to the upper pressure head 14;

step 3: open the water pressure loading controller 42 to add water, so that the water passes vertically through the lower permeable stone 23, the rock sample 9, and the upper permeable stone 22 from the water inlet, and passes horizontally through the rock sample 9 and the water-permeable pressure hoop 10 to achieve three-dimensional immersion of the rock sample 9, open the exhaust port 35 to allow water flowing in for some time, and close the exhaust port 35 when there is no residual air in the triaxial high-temperature and high-pressure reaction chamber 40;

step 4: set the axial pressure, water pressure and temperature according to the test plan, and carry out the swelling rate test of the rock sample 9 under different axial pressure, confining pressure, water pressure and temperature coupling conditions.

Specifically, different types of swelling tests are described:

I. Lateral Restraint Swelling Rate Test:

step 1: open the upper end cover 1, take out the upper pressure head 14 and the upper limit sleeve 21, process the water-permeable pressure hoop 10, use high-strength glue to bond the multiple sections of hoop bodies 18 with joints to achieve complete lateral volume constraint of the rock sample 9, and then install the rock sample 9, the upper permeable stone 22, the upper limit sleeve 21, the upper pressure head 14 and the upper end cover 1 in sequence; adjust the triaxial high-temperature and high-pressure reaction chamber 40 to the appropriate position of the operating table 37, that is, the upper pressure head 14 is aligned with the axial pressure loading screw pressure head 17;

step 2: turn off the confining pressure loading controller 41 and seal the oil inlet 33 and the oil outlet 34, and calibrate the axial pressure loading controller 44, the temperature controller 43 and the water pressure loading controller 42;

step 3: turn on the water pump, and water enters from the water pipe 48 and then vertically enters the water inlet pipe 15, the lower permeable stone 23, the rock sample 9, and the upper permeable stone 22, and then horizontally passes through the rock sample 9 and the water-permeable pressure hoop 10, so as to realize three-dimensional immersion of the rock sample 9; start the axial pressure loading controller 44, the water pressure loading controller 42, the temperature controller 43, the pH value monitor 45, and the data acquisition and analyzer 46;

step 4: open the exhaust port 35 to allow water flowing in constantly without water pressure for 5 minutes, and close the exhaust port 35 when there is no residual air in the reaction chamber. Use the axial pressure loading screw pressure head 17 to load the rock sample 9 with axial pressure, use the sealing liner sleeve 4 and the water-permeable pressure hoop 10 to isolate the rock sample 9 from the oil and water environment, set the axial pressure, water pressure and temperature according to the test plan, carry out the lateral constraint swelling rate test of the rock sample 9, use the axial sensor 36 and four lateral circumferential stress-strain sensors 12 to measure the axial deformation, stress and radial stress of the sample, use the ion concentration sensor in the reaction chamber to obtain the transport path of ions after dissolution, and use the pH value monitor 45 to obtain the law of changes in water acidity and alkalinity caused by dissolution.

II. Swelling Test Under Different Confining Pressure and Water Pressure Conditions:

step 1: open the upper end cover 1 and take out the upper pressure head 14. Because the rock sample 9 does not need lateral constraints, there is no need to bond the hoop bodies 18 with joints of the water-permeable pressure hoop 10. Then install the rock sample 9, the upper permeable stone 22, the upper pressure head 14, and the upper end cover 1 in sequence, and adjust the triaxial high-temperature and high-pressure reaction chamber 40 to the appropriate position of the operating table 37, that is, the upper pressure head 14 is aligned with the axial pressure loading screw pressure head 17;

step 2: calibrate the water pressure loading controller 42, the confining pressure loading controller 41, the temperature controller 43 and the axial pressure loading controller 44;

step 3: turn on the water pump. Water enters from the water pipe 48 and then vertically enters the water inlet pipe 15, the lower permeable stone 23, the rock sample 9, and the upper permeable stone 22 in sequence. It then passes through the rock sample 9 and the water-permeable pressure hoop 10 in sequence in the horizontal direction to achieve three-dimensional immersion of the rock sample 9. The axial pressure loading controller 44, the water pressure loading controller 42, the temperature controller 43, the pH value monitor 45, and the data acquisition and analyzer 46 are started.

step 4: open the exhaust port 35 to allow water flowing in constantly without water pressure for 5 minutes, and close the exhaust port 35 when there is no residual air in the reaction chamber. Set the axial pressure, water pressure and temperature according to the test plan, carry out the swelling rate test of the rock sample 9 under different confining pressure, water pressure and temperature coupling conditions, use the axial sensor 36 and four lateral circumferential stress-strain sensors 12 to measure the axial deformation, stress and radial deformation and stress of the sample, use the ion concentration sensor in the reaction chamber to obtain the transport path of ions after dissolution, and use the pH value monitor 45 to obtain the law of changes in water acidity and alkalinity caused by dissolution.

The lateral constraint swelling rate test and the swelling test under different confining pressure and water pressure conditions are mainly aimed at simulating the swelling and deformation law of chemical swelling rock in complex environment, while the free swelling rate test is aimed at the swelling and deformation law of chemical swelling rock in natural environment, and fewer restrictive conditions are required. Therefore, when conducting the free swelling rate test, it is necessary to take out the sealing liner sleeve 4, the water-permeable pressure hoop 10, the force transmission pad 8 and the upper limit sleeve 21, and make the displacement rod 25 directly contact the rock sample 9 to realize the free swelling of the rock sample 9 in the internal cavity, and carry out the free swelling rate test.

The above is a detailed description of the specific embodiments of the present invention in conjunction with the drawings, but the present invention is not limited to the described embodiments. For those skilled in the art, various changes, modifications, substitutions and variations of these embodiments are made without departing from the principles and spirit of the present invention, and still fall within the scope of protection of the present invention.

We claim:

1. A three-dimensional water-absorption swelling multifunctional experimental machine for chemical swelling rocks, characterized in that it comprises a triaxial high-temperature and high-pressure reaction chamber, wherein the triaxial high-temperature and high-pressure reaction chamber is respectively connected to a confining pressure loading controller, a water pressure loading controller, a temperature controller, an axial pressure loading controller, a pH value monitor and a data acquisition and analyzer;

the triaxial high-temperature and high-pressure reaction chamber comprises an upper end cover and a lower end cover which are detachable at upper and lower ends; an internal cavity and an external cavity are provided between the upper end cover and the lower end cover; the external cavity is sleeved outside the internal cavity; a sealing liner sleeve is provided between the internal cavity and the external cavity; an upper convex body and a lower convex body protruding toward one side of the external cavity are provided at upper and lower ends of the sealing liner sleeve; an oil cavity is provided between the upper convex body and the lower convex body; and force transmission pads are provided between the upper convex body and the upper end cover and between the lower convex body and the lower end cover;

a rock sample is provided in the internal cavity, and a water-permeable pressure hoop is arranged outside the rock sample, the outer wall of the water-permeable pressure hoop is in close contact with the sealing liner sleeve, and the sealing liner sleeve is connected to a circumferential stress-strain sensor via a displacement structure; an upper pressure head is arranged above the rock sample, a water outlet pipe connected to the rock sample is arranged in the upper pressure head, a lower pressure head is arranged below the rock sample, a water inlet pipe connected to the rock sample is arranged in the lower pressure head, and an axial pressure loading screw pressure head is detachably connected to the top of the upper pressure head; the water-permeable pressure hoop comprises a plurality sections of hoop bodies with joints, and the hoop bodies are respectively provided with axial water-passing grooves and radial water-passing holes;

the displacement structure comprises a compression cavity, holes are provided at both ends of the compression cavity, a displacement rod is provided in the compression cavity, both ends of the displacement rod extend out of the holes, one end of the displacement rod is in close contact with the sealing liner sleeve, and the other end is connected to the circumferential stress-strain sensor via a connecting plate, a portion of the displacement rod located in the compression cavity is provided with a convex body and a force adjustment spring, the convex body is located on the side close to the sealing liner sleeve, the force adjustment spring is sleeved on the non-convex body portion of the displacement rod, and the outer diameter of the convex body is greater than the radial dimension of the hole.

2. The three-dimensional water-absorption swelling multifunctional experimental machine for chemical swelling rocks according to claim 1, characterized in that: an upper limit sleeve is movably connected between the upper pressure head and the sealing liner sleeve, the upper limit sleeve corresponds to the water-permeable pressure hoop up and down and extends upward to the upper end cover, and a lower limit sleeve is movably connected between the lower pressure head and the sealing liner sleeve, and the lower limit sleeve extends downward to the lower end cover.

3. The three-dimensional water-absorption swelling multifunctional experimental machine for chemical swelling rocks according to claim 2, characterized in that: the upper pressure head extends out of the upper end cover, an upper permeable stone is provided between the upper pressure head and the rock sample, and a lower permeable stone is provided between the lower pressure head and the rock sample; one end of the water outlet pipe is connected to the upper permeable stone, and the other end is connected to the pH value monitor through a first flow meter and a first fluid pressure gauge; one end of the water inlet pipe is connected to the lower permeable stone, and the other end is connected to the water pressure loading controller and the water pump through a second flow meter and a second fluid pressure gauge.

4. The three-dimensional water-absorption swelling multifunctional experimental machine for chemical swelling rocks according to claim 3, characterized in that: an oil inlet and an oil outlet are arranged opposite each other on the outer wall of the triaxial high-temperature and high-pressure reaction chamber, the oil inlet and the oil outlet are internally connected to the oil cavity, and the oil inlet and the oil outlet are externally connected to the confining pressure loading controller; and an exhaust port communicating with the outside is arranged on the external cavity.

5. The three-dimensional water-absorption swelling multifunctional experimental machine for chemical swelling rocks according to claim 4, characterized in that: the axial pressure loading screw pressure head is connected to the axial pressure loading controller, the axial pressure loading screw pressure head is arranged above the upper pressure head through a reaction frame, the axial pressure loading screw pressure head is also connected to an axial sensor, and the axial sensor is connected to the data acquisition and analyzer.

6. The three-dimensional water-absorption swelling multifunctional experimental machine for chemical swelling rocks according to claim 5, characterized in that: the experimental machine also comprises an operating table, on which a feeding pad is detachably fixed, and the feeding pad is arranged below the triaxial high-temperature and high-pressure reaction chamber by connecting with the lower end cover, and a moving wheel is provided at the lower part of the feeding pad; the reaction frame is fixed on the operating table.

7. The experimental method of the three-dimensional water-absorption swelling multifunctional experimental machine for chemical expansion rocks according to claim 6, characterized in that it comprises the following steps:
   step 1: process the water-permeable pressure hoop according to the swelling test type of the rock sample: when conducting a lateral restraint swelling rate test, use high-strength glue to bond the multiple sections of the hoop bodies with joints; when conducting a free swelling rate test and a swelling test under different confining pressure and water pressure conditions, there is no need to process the water-permeable pressure hoop;
   step 2: place the triaxial high-temperature and high-pressure reaction chamber containing the rock sample below the axial pressure loading screw pressure head through the feeding pad, so that the axial pressure loading screw pressure head is aligned with the upper pressure head;
   step 3: open the water pressure loading controller to add water, so that the water passes vertically through the lower permeable stone, the rock sample, and the upper permeable stone from the water inlet pipe, and passes horizontally through the rock sample and the water-permeable pressure hoop to achieve three-dimensional immersion of the rock sample, open the exhaust port, and close the exhaust port when there is no residual air in the triaxial high-temperature and high-pressure reaction chamber;
   step 4: set the axial pressure, water pressure and temperature according to the test plan, and carry out the swelling rate test of the rock sample under different axial pressure, confining pressure, water pressure and temperature coupling conditions.

8. The three-dimensional water-absorption swelling multifunctional experimental machine for chemical swelling rocks according to claim 1, characterized in that: an annular ion concentration sensor and a heating coil are sleeved over the rock sample, the heating coil is connected to the temperature controller, and the annular ion concentration sensor and the circumferential stress-strain sensor are connected to the data acquisition and analyzer.

9. The three-dimensional water-absorption swelling multifunctional experimental machine for chemical swelling rocks according to claim 1, characterized in that: the displacement structures are provided in plurality, the circumferential stress-strain sensor corresponds to the displacement structures one by one, and the plurality of displacement structures are evenly distributed circumferentially on the side wall of the sealing liner sleeve.

* * * * *